United States Patent
Wang et al.

(10) Patent No.: US 8,258,176 B2
(45) Date of Patent: Sep. 4, 2012

(54) DITHIOLOPYRROLONE COMPOUNDS, THE PREPARATION AND THE USE THEREOF

(75) Inventors: Guoping Wang, Shanghai (CN); Quanhai Liu, Shanghai (CN); Haiyan Sun, Shanghai (CN); Wei Wu, Shanghai (CN); Jian Hou, Shanghai (CN); Lin Yao, Shanghai (CN); Chungang Li, Shanghai (CN); Minyu Liu, Shanghai (CN); Fei Li, Shanghai (CN); Xuejun Wu, Shanghai (CN); Shuai Zhao, Shanghai (CN)

(73) Assignees: Shanghai Institute of Pharmaceutical Industry, Shanghai (CN); Shanghai Modern Pharmaceutical Co., Ltd., Shanghai (CN)

( * ) Notice: Subject to any disclaimer, the term of this patent is extended or adjusted under 35 U.S.C. 154(b) by 146 days.

(21) Appl. No.: 12/676,470

(22) PCT Filed: Aug. 29, 2008

(86) PCT No.: PCT/CN2008/072207
§ 371 (c)(1),
(2), (4) Date: Mar. 4, 2010

(87) PCT Pub. No.: WO2009/033396
PCT Pub. Date: Mar. 19, 2009

(65) Prior Publication Data
US 2010/0210856 A1    Aug. 19, 2010

(30) Foreign Application Priority Data
Sep. 5, 2007 (CN) .......................... 2007 1 0045600

(51) Int. Cl.
*A61K 31/407* (2006.01)
*C07D 487/04* (2006.01)
*C07D 487/02* (2006.01)

(52) U.S. Cl. ........................................ 514/421; 548/453
(58) Field of Classification Search .................. 548/453; 514/421
See application file for complete search history.

(56) References Cited

U.S. PATENT DOCUMENTS
2006/0074125 A1    4/2006   Chen et al.

FOREIGN PATENT DOCUMENTS
| CN | 1642959 A | 7/2005 |
|---|---|---|
| GB | 2170498 A | 8/1986 |
| JP | 63284181 A | 11/1988 |
| WO | 9912543 A1 | 3/1999 |
| WO | 0220767 | 3/2002 |
| WO | WO 2008038175 A2 * | 4/2008 |

OTHER PUBLICATIONS

ISR for PCT/CN2008/072207 dated Dec. 4, 2008.
Chinese Office Action for Application No. 200710045600.X mailed Apr. 14, 2011.
Supplemental European Search Report for Application No. 08800719.0 mailed May 2, 2011.

* cited by examiner

*Primary Examiner* — Jason M Nolan
(74) *Attorney, Agent, or Firm* — Lowe, Hauptman, Ham & Berner, LLP

(57) ABSTRACT

The invention discloses a dithiolopyrrolone compound represented by formula I or its pharmaceutically acceptable salts, wherein $X_1$, $R_1$, $R_2$, $R_3$, $R_4$ are defined as in the description. The invention also discloses the preparation of such compounds, and the use of such compounds in preparation of medicaments for increasing peripheral white blood cells and in preparation of ancillary medicaments for inhibiting the decrease of peripheral white blood cells in radiotherapy or chemotherapy.

24 Claims, No Drawings

DITHIOLOPYRROLONE COMPOUNDS, THE PREPARATION AND THE USE THEREOF

RELATED APPLICATIONS

The present application is national phase of PCT/CN2008/072207 filed Aug. 29, 2008, and claims priority from Chinese Application Number 200710045600.X filed Sep. 5, 2007, the disclosures of which are hereby incorporated by reference herein in their entirety.

FIELD OF THE INVENTION

This invention relates to a new class of compounds and their preparation methods and the use thereof, specifically involving the dithiolopyrrolone compounds and their preparation methods, and application in the field of medicine thereof.

BACKGROUND OF THE INVENTION

Leucopenia is a common clinical disease, and severe leucopenia can lead to the occurrence of severe infection and even death. Therefore, leucopenia in the clinic leucopenia, especially severe leucopenia was given full attention.

Leucopenia may be primary, hereditary, can also be secondary to infection and other factors, but in the clinic leucopenia induced by chemical substances, drugs, in particular cytotoxic drugs and radiotherapy is more common.

Malignant tumor is one of the most major diseases that affect human health and life. Chemotherapy, radiotherapy and surgical treatment are combinationally used as the primary means of treating malignant tumor. Cytotoxic drugs are still dominant in the cancer chemotherapy drugs at this stage. As the selectivity of such drugs is not strong, the vast majority of them all have different degrees of inhibition of the bone marrow. At present, the impact of high-dose chemotherapy, as well as multi-cycle multi-drug combinational chemotherapy for malignant tumor is widely used, which makes bone marrow suppression very common. According to the statistics, 90% of chemotherapy patients have the phenomenon of varying degrees reduction of white blood cells. The reduction of white blood cells becomes the limiting toxicity of chemotherapy drugs dose, which is the important reason of not increasing chemotherapy dose of many patients, thus directly affecting the increasing of index of chemotherapy. And the reduction of peripheral white blood cells caused by bone marrow suppression which is induced by radiotherapy is the most common and most serious complications.

These factors reduce the peripheral white blood cells, whose pathogenesis is mainly the direct injury of the hematopoietic stem cells or progenitor cells and the early cell of division phase, as well as the interference of the proliferating cycle of granulocyte. Because the half-life of the granulocyte is short and the granulocyte is updated quickly, the granulocyte showed first the reduction for the drug of bone marrow suppression. In addition, certain factors can still induce the mature barriers of stem cells or progenitor cells, can also cause granulocyte damage or consume excessively by immunological factors or non-immunological factors. There are a small number of diseases which cause neutropenia phenomenon by the expansion of granulocyte-edge pool, or the release barriers and other mechanisms.

In the clinical treatment of leucopenia, in addition to the general robustness therapy, infection control, infusion of granulocytes if necessary, the most important method is the application of drug preventing and treating the bone marrow suppression, and promoting the peripheral leukocytosis. Therefore, the class of drug has long been the hot content of the research of new drug in the world.

There are many different types of clinical medicine to stimulate the growth of white blood cells, such as vitamin B4, vitamin B6, lithium carbonate, Leucogen, shark liver alcohol, creatinine, and coenzyme A and so on. However, a large number of clinical practices proved that the efficacy of these drugs are not sure, and most are temporary, the efficacy is very little for severe neutropenia induced by radiotherapy and chemotherapy. Currently in the leucocyte-stimulating drugs with considered curative effect and rapid efficacy, only granulocyte colony-stimulating factor (G-CSF) and granulocyte-macrophage colony-stimulating factor (GM-CSF) play a major role in the cancer radiotherapy and chemotherapy.

But G-CSF and GM-CSF are protein peptide drugs produced through genetic engineering approaches. The disadvantages include the inconvenience of storage and transportation, easy inactivation to affect the efficacy, shorter half-life, sometimes even twice a day injection, which gives some patients great inconvenience, and more expensive price. Therefore, it has important significance to develop small molecule compounds with prevention and treatment of bone marrow suppression, promotion of leukocytosis, curative effect, and rapid efficacy.

The dithiolopyrrolone compounds are a class of 1,2-dithioleheterocyclicpentene[4,3-b]pyrrole-5(4H)-one ring compounds. The naturally occurring dithiolopyrrolone compounds have been proven to have antibacterial activity, as well as the antitumor activity. The compounds with improved structural characteristics have been reported in the literature. Webster, etc. (U.S. Pat. No. 6,020,360, WO99/12543), Godfrey and Dell (GB2170498), Kawada Shuji, etc. (JP63-284181, JP11-279179), Stachel, etc. (Helvetica Chimica Acta 2002, 85, 4453), and Webster, etc. (WO2003/080624) reported a number of dithiolopyrrolone compounds through chemical synthesis and their antibacterial and antitumor activity.

SUMMARY OF THE INVENTION

It is an object of the present invention to provide a new class of small molecule pharmaceutically active compound and pharmaceutical composition, preparation methods, and the use in the field of leucocyte-stimulating medicine, which solves the technical problem that the efficacy of most leucocyte-stimulating drugs is not well, while protein peptide drugs such as G-CSF and GM-CSF with better efficacy have the disadvantages including the inconvenience of storage and transportation, easy inactivation, shorter half-life, the inconvenience of use, and expensive price.

The small molecule pharmaceutically active compounds of the invention relates to dithiolopyrrolone compounds (Formula I) and their pharmaceutical acceptable salts:

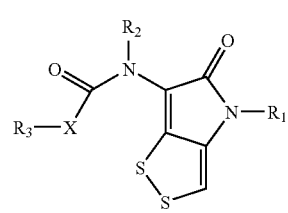

I

Wherein, X is O, $NR_4$ or S;

$R_1$ represents unsubstituted or optionally substituted following groups: $C_3$-$C_8$ cycloalkyl, $C_5$-$C_{10}$ aryl or three to ten-membered heterocyclic group having one to three heteroatoms independently selected from N, O or S;

$R_2$ represents hydrogen or $C_1$-$C_{10}$ alkyl;

$R_3$ represents hydrogen, or unsubstituted or optionally substituted following groups: $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkyl substituted by $C_5$-$C_{10}$ aryl, $C_5$-$C_{10}$ aryl, or three to ten-membered heterocyclic having one to three heteroatoms independently selected from N, O or S;

$R_4$ represents hydrogen or $C_1$-$C_{10}$ alkyl.

Wherein, one or more substituted groups connected with optionally substituted groups mentioned above may be selected from the following groups: $C_1$-$C_6$ alkyl, $C_1$-$C_6$ alkoxyl, $C_1$-$C_6$ alkylthio, halogen, $C_1$-$C_6$ alkoxycarbonyl, $C_1$-$C_6$ alkoxymethyl, aminomethyl, $NH_2$, NH ($C_1$-$C_6$ alkyl), N($C_1$-$C_6$ alkyl)$_2$ and nitro group.

Wherein, preferably $R_1$ is unsubstituted or optionally substituted following groups: $C_5$-$C_{10}$ aryl or five to ten-membered aromatic heterocyclic group having one to three heteroatoms independently selected from N, O or S, more preferably is unsubstituted or optionally substituted phenyl, and further preferably is 2,4-substituted phenyl with $C_1$-$C_6$ alkyl or $C_1$-$C_6$ alkoxyl, the most preferably $R_1$ is 2,4-dimethoxy phenyl or 2-methyl phenyl.

Wherein, preferably $R_2$ is hydrogen.

Wherein, preferably $R_3$ is unsubstituted or optionally substituted following groups: $C_1$-$C_{10}$ alkyl, $C_2$-$C_{10}$ alkenyl, $C_1$-$C_{10}$ alkyl with phenyl, phenyl, $C_3$-$C_{10}$ cycloalkyl or five to ten-membered aromatic heterocyclic group having one to three heteroatoms independently selected from N, O or S; more preferably is pyridyl, pyridazinyl, pyrimidinyl, $C_1$-$C_{10}$ alkyl with furyl, $C_1$-$C_{10}$ alkyl with thienyl, $C_1$-$C_6$ alkyl with pyrrolyl, or $C_1$-$C_{10}$ alkyl with pyranyl.

Unless otherwise indicated, the following terms appeared in the description and claims of the invention have the following meanings:

As used herein, the term "alkyl" refers to the branched-chain and straight-chain saturated aliphatic alkyl with the specified number of carbon atoms. For example, $C_1$-$C_{10}$ in "$C_1$-$C_{10}$ alkyl" is defined as straight-chain or branched-chain structure with 1, 2, 3, 4, 5, 6, 7, 8, 9 or 10 carbon atoms. For example, "$C_1$-$C_{10}$ alkyl" specifically includes methyl, ethyl, propyl, isopropyl, n-butyl, tert-butyl, isobutyl, pentyl, hexyl, heptyl, octyl, nonyl, and decyl, and so on.

The term "alkoxy" refers to the cyclic or non-cyclic alkyl connected by oxygen-bridge with the specified number of carbon atoms. Thus, "alkoxy" includes the definitions of above alkyl and cycloalkyl.

The term "alkenyl" refers to the straight chain, branched-chain or cyclic non-aromatic alkyl containing at least one carbon-carbon double bond with a specified number of carbon atoms. Preferably is the existence of a carbon-carbon double bond, and up to four non-aromatic carbon-carbon double bonds. Thus, "$C_2$-$C_{10}$ alkenyl" refers to the alkenyl with 2-10 carbon atoms. "$C_2$-$C_6$ alkenyl" refers to the alkenyl with 2-6 carbon atoms, including vinyl, propenyl, butenyl, 2-methyl-butenyl and cyclohexenyl. The straight-chain, branched-chain or ring section of alkenyl can contain a double bond, and can be substituted if indicated as substituted alkenyl.

The term "alkynyl" refers to the straight chain, branched-chain or cyclic alkyl containing at least one carbon-carbon triple bond with a specified number of carbon atoms. Wherein, there may be up to three carbon-carbon triple bonds. Thus, "$C_2$-$C_{10}$ alkynyl" refers to the alkynyl with 2-10 carbon atoms. "$C_2$-$C_6$ alkynyl" refers to the alkynyl with 2-6 carbon atoms, including ethynyl, propynyl, butynyl and 3-methyl butynyl, and so on.

The term "cycloalkyl" refers to saturated or partially unsaturated monocyclic, polycyclic or bridged carbocyclic substituent. Cycle with 3-20 carbon atoms can be expressed as $C_{3-20}$ cycloalkyl; Cycle with 5-15 carbon atoms can be expressed as $C_{5-15}$ cycloalkyl; Cycle with 3-8 carbon atoms can be expressed as $C_{3-8}$ cycloalkyl; and so on. The term includes, but is not limited to, cyclopropyl, cyclobutyl, cyclopentyl, cyclohexyl, cycloheptyl, cyclooctyl, 1H-indenyl, 2,3-dihydroindenyl, 1,2,3,4-tetrahydronaphthyl, 5,6,7,8-tetrahydronaphthyl, 8,9-dihydro-7H-benzocycloheptenyl, 6,7,8,9-tetrahydro-5H-benzocycloheptenyl, 5,6,7,8,9,10-hexahydro-benzocyclooctenyl, fluorenyl, bicyclo[2.2.1]heptyl, bicyclo [2.2.1]heptenyl, bicyclo[2.2.2]octyl, bicyclo[3.1.1]heptyl, bicyclo[3.2.1]octyl, bicyclo[2.2.2]octenyl, bicyclo[3.2.1] octenyl, Adamantyl, octahydro-4,7-methylene-1H-indenyl and octahydro-2,5-methylene-pentalene, and so on. Cycloalkyl substituents can be connected to the central molecule by any suitable carbon atoms, and can be further substituted when permitted.

As used herein, the term "aryl" refers to any stable monocyclic or bicyclic carbon ring with up to seven atoms in each ring, including at least one aromatic ring. Examples of aryl unit mentioned above include phenyl, naphthyl, tetrahydronaphthyl, 2,3-dihydro indenyl, biphenyl, phenanthryl, anthryl or acenaphthyl. Understandably, the connection is carried out through the aromatic ring when the aryl substituent is the bicyclic substituent, in which one cycle is non-aromatic ring.

As used herein, the term "heteroaryl" refers to any stable monocyclic or bicyclic ring with up to seven atoms in each ring, including at least one aromatic ring and one to four heteroatoms selected from O, N, and S. The heteroaryl in the definition includes, but is not limited to: acridinyl, carbazolyl, cinnolinyl, quinoxalinyl, pyrazolyl, indolyl, benzotriazolyl, furyl, thienyl, benzothienyl, benzofuranyl, quinolyl, isoquinolyl, oxazolyl, isooxazolyl, indolyl, pyrazinyl, pyridazinyl, pyridyl, pyrimidinyl, pyrrolyl, tetrahydroquinolinyl. Same as the definition of heterocycle below, "heteroaryl" also should be understood to include any N-oxide derivatives containing aza-aryl. Understandably, the connection is carried out through the aromatic ring or ring containing heteroatom when the heteroaryl substituent is the bicyclic substituent, in which one cycle is non-aromatic ring or does not contain heteroatom.

As used herein, the term "heterocycle" or "heterocyclic" refers to five to ten-membered aromatic or non-aromatic heterocycle containing one to four heteroatoms selected from O, N and S, and bicyclic group. Therefore, the "heterocyclic" includes the heteroaryl mentioned above as well as their dihydro or tetrahydro analogs. Other Examples of "heterocyclic" include, but are not limited to the following: benzimidazolyl, benzofuranyl, benzo, benzopyrazolyl, benzotriazolyl, benzothienyl, benzooxazolyl, carbazolyl, carbolinyl, cinnolinyl, furanyl, imidazolyl, dihydroindolyl, indolyl, indazolyl, isobenzofuranyl, isoazaindenyl, isoquinolinyl, isothiazolyl, isoxazolyl, naphthalene pyrimidinyl, oxadiazolyl, oxazolyl, oxazolinyl, isooxazolinyl, oxycyclobutyl, pyranyl, pyrazinyl, pyrazolyl, pyridazinyl, pyridopyridyl, pyridazinyl, pyridyl, pyrimidinyl, pyrrolyl, quinazolinyl, quinolyl, quinoxalinyl, tetrahydropyranyl, tetrazolyl, tetrazopyridyl, thiadiazolyl, thiazolyl, thienyl, triazolyl, azacyclobutyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuryl, dihydroimidazole, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazacyclobutyl, methylenedioxybenzoyl, tetrahydrofuranyl and tetrahydrothienyl and the N-oxide. Heterocyclic substituent may be connected by carbon atom or heteroatom.

The present invention, preferably the described pharmaceutical acceptable salt is the salt from the reaction of dithiolopyrrolone compounds and pharmaceutical acceptable acid, or from the reaction of dithiolopyrrolone compounds having the acidic group and alkaline compounds. Wherein, preferably the acid described is selected from inorganic acid (such as hydrochloric acid, sulfuric acid, phosphoric acid or hydrobromic acid, etc.), and organic acids (such as oxalic acid, maleic acid, fumaric acid, malic acid, tartaric acid, citric acid, or benzoic acid, etc.); preferably the alkaline compounds described is selected from sodium hydroxide, potassium hydroxide, calcium hydroxide, sodium carbonate or potassium bicarbonate. For example, 6-amino-4-(2-methylphenyl)-4H-[1,2]dithioleheterocyclicpentene[4,3-b]-5-pyrrolidine one hydrochloride salt. The pharmaceutical acceptable salt mentioned above is easy to be separated, can be purified by conventional separation methods, such as solvent extraction, dilution, recrystallization, column chromatography and thin-layer preparation chromatography, etc.

The invention is also related to two preparation methods of dithiolopyrrolone compounds shown as formula I in this invention.

Method 1: reaction can be carried out between the compound shown as formula I-6 and chloroformate or chlorine formamide via the organic base in the non-protonic solvent.

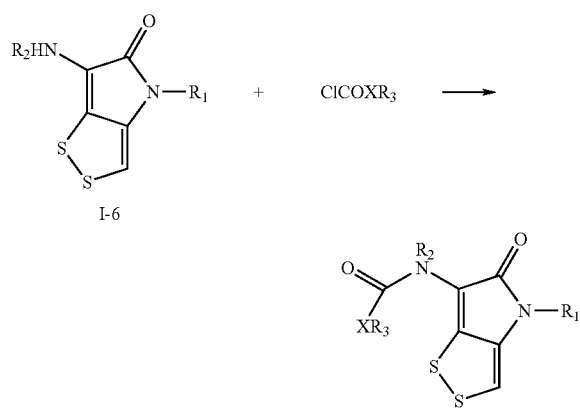

Wherein, X, $R_1$, $R_2$, $R_3$ and $R_4$ are the same as the definition mentioned above.

Wherein, the molar ratio of the compound shown as formula I-6 and chloroformate (X=O) or chlorine formamide (X=$NR_4$, $R_4$=hydrogen or alkyl) is preferably 1:1~1:10, more preferably is 1:1.2~1:1.5; the organic base described can be selected from the conventional tertiary amines in the field, such as triethylamine, pyridine and N,N-dimethyl aniline, etc., more preferably is the triethylamine and/or pyridine; the molar ratio of organic base and I-6 is preferably 2~4:1; the non-protonic solvent described can be selected from the conventional non-protonic solvent in the field, such as halogenated hydrocarbons, including dichloromethane, 1,2-dichloroethane, chloroform; ketones, such as acetone, butanone; amides, such as N,N-dimethylformamide, N,N-dimethylacetamide; ethers, such as tetrahydrofuran; more preferably is tetrahydrofuran, the usage of non-protonic solvent is preferably 1~100-fold of the weight of I-6; the reaction described is preferred preferably at the temperature between −20 and 50° C., more preferably between −5 and 20° C. The reaction time can be controlled by TLC.

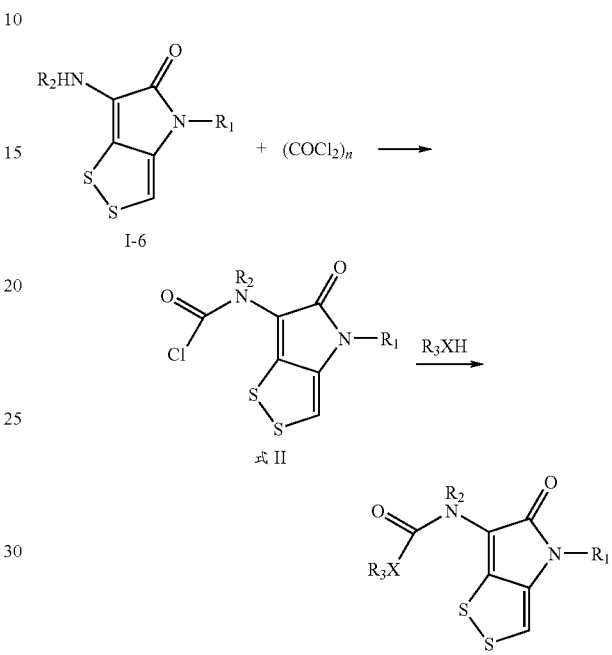

Method 2:

(1) Compound shown as formula II was prepared from the reaction between the compound shown as formula I-6 and carbonyl chloride (phosgene) or bis(trichloromethyl)carbonate (triphosgene) via the organic base in the non-protonic solvent.

(2) Reaction can be carried out between the compound shown as formula II and $R_3XH$ via the organic base in the non-protonic solvent.

Wherein, X, $R_1$, $R_2$, $R_3$ and $R_4$ are the same as the definition mentioned above, n is one or three.

Wherein, in step 1 the molar ratio of the compound shown as formula I-6 and carbonyl chloride (phosgene) or bis (trichloromethyl)carbonate (triphosgene) is preferably 1:1~1:10, more preferably is 1:1.2~1:1.5; the usage of $R_3XH$ is preferably 1~10-folds of the molar amount of I-6, more preferably is 1.2~2-folds; in step (1) and/or step (2), the organic base described can be selected from the conventional tertiary amines in the field, such as triethylamine, pyridine and N,N-dimethyl aniline, etc., more preferably is triethylamine and/or pyridine; organic base can be added once at a time in step (1), or added again in the step (2), the molar ratio of the total amount of the organic base and I-6 is 1:1~1:10; the non-protonic solvent described can be selected from the conventional non-protonic solvent in the field, such as halogenated hydrocarbons, including dichloromethane, 1,2-dichloroethane, chloroform; ketones, such as acetone, butanone; amides, such as N,N-dimethylformamide, N, N-dimethylacetamide; ethers, such as tetrahydrofuran; more preferably is tetrahydrofuran, the usage of non-protonic solvent is preferably 1~100-folds of the weight of I-6; in step (1) and/or step (2), the reaction described is preferably performed at the temperature between −20 and 50° C., more preferably between −5 and 20° C. The reaction time can be controlled by TLC.

In the above two methods, the described compound shown as formula I-6 can be prepared by the method described in GB2170498. Here is an example: compound I-1 is prepared by the nucleophilic substitution reaction between 1,3-dichloroacetone as the starting material and tert-butyl mercaptan via the base (eg potassium carbonate) in the non-protonic solvent (eg acetone). Then, schiff base obtained without purifying from the reaction of compound I-1 and amines (eg 2,4-dimethoxy-aniline) catalyzed by the acid (eg p-toluenesulfonic acid), directly reacts with oxalyl chloride and triethylamine to get compound I-2. Later, compound I-3 is prepared by the reaction that compound I-2 is ammoniated with the required amine (eg methylamine) at a high temperature (eg 150° C.) in the non-reactive organic acid (such as butyric acid). Then, the amino group of compound I-3 is protected with trifluoro-acetic anhydride to get compound I-4. In polar solvent (eg acetonitrile), compound I-5 is prepared from compound I-4 by deprotecting with mercury salt (eg mercuric acetate), removing mercury with hydrogen sulfide, and oxidation reaction with oxidant (such as iodine). Finally, in polar solvent (eg methanol), the compound shown as formula I-6 can be obtained from the compound I-5 by hydrolyzing trifluoroacetyl group with acid (eg hydrochloric acid). The reaction scheme is as follows:

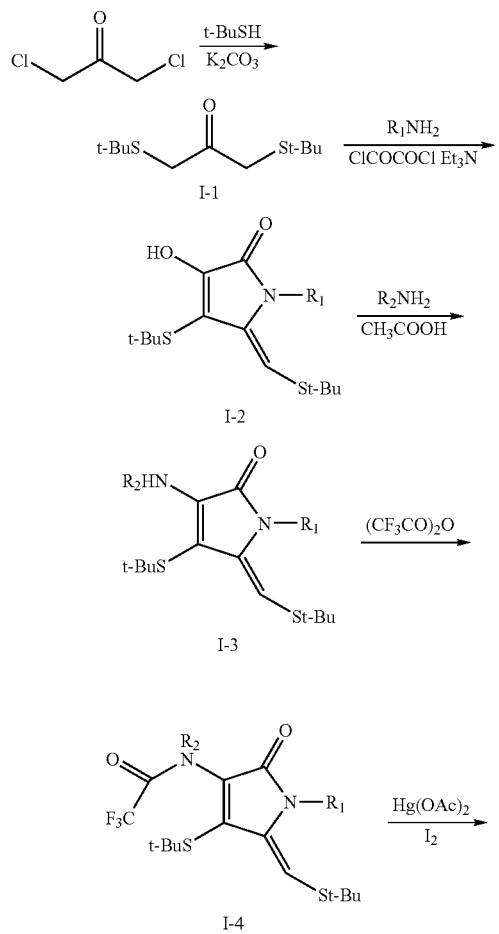

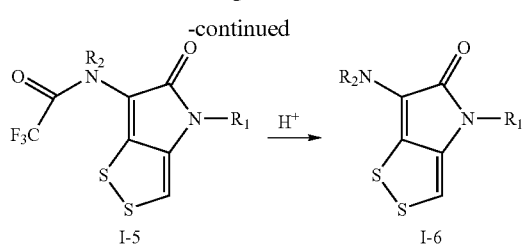

In method 1, the described chloroformate or chlorine formamide may be obtained according to the following conventional methods:

$R_3XH + (COCl_2)_n \rightarrow ClCOXR_3$

Reaction can be carried out between $R_3XH$ and equimolar or slightly excessive phosgene or triphosgene via the organic base (eg triethylamine) at the temperature between −20 and 50° C. in the non-protonic solvent (eg tetrahydrofuran).

Wherein, n=1 or 3, X and $R_3$ are same as the definition mentioned above. Chloroformate may also be purchased commercially.

The present invention is also related to the pharmaceutical compositions which contain dithiolopyrrolone compounds shown as formula I in this invention or pharmaceutically acceptable salts thereof.

The pharmaceutical compositions can be prepared from the compounds of the present invention with all types of pharmaceutical additives (eg the diluent and excipient, etc.). According to therapeutic purposes, pharmaceutical compositions can be made to be various types of drug delivery unit formulations such as tablets, pills, powders, liquids, suspensions, emulsion, granules, capsules, suppositories and injections (solutions and suspensions), etc.

In order to make pharmaceutical composition form the tablets, any known and widely used excipients in the present field can be used. For example, the carriers, such as lactose, sugar, sodium chloride, glucose, urea, starch, calcium carbonate, kaolin, crystalline cellulose and silicic acid, etc.; adhesives, such as water, ethanol, propanol, ordinary syrup, glucose solution, starch solution, gelatin solution, carboxymethyl cellulose, shellac, methyl cellulose and potassium phosphate, polyvinylpyrrolidone, etc.; disintegrating agents, such as dry starch, sodium alginate, agar powder, and kelp powder, sodium bicarbonate, calcium carbonate, fatty acid ester of polyethylene dehydrated sorbitol, sodium lauryl sulfate, stearic acid monoglyceride, starch and lactose, etc.; disintegration inhibitors, such as sugar, glycerol tristearate, coconut oil and hydrogenated oil; absorption enhancers, such as quaternary ammonium base and sodium lauryl sulfate, etc.; wetting agents, such as glycerol, starch, etc.; adsorbents, such as starch, lactose, kaolin, bentonite and colloidal silicic acid, etc.; as well as lubricants, such as pure talc, stearic acid salts, boric acid powder and polyethylene glycol. If necessary, the tablets can be prepared as the sugar-coated tablets, gelatin film-coated tablets, casing tablets, film-coated tablets, double film-coated tablets and multi-films-coated tablets by usual coating material.

In order to make the form of pill's form of pharmaceutical composition, any known and widely used excipients in this field may be used, for example, carriers, such as lactose, starch, coconut oil, hardened vegetable oil, kaolin and talc, etc.; adhesives, such as the arabic gum powder, yellow with powder, gelatin and ethanol, etc.; disintegrating agents, such as agar, and kelp powder.

In order to make the form of suppository form of pharmaceutical composition, any known and widely used excipients maybe used, for example, polyethylene glycol, coconut oil, higher alcohols, ester of higher alcohol, gelatin and semi-synthetic glyceride, etc.

To prepare injection form of pharmaceutical composition, solution and suspension maybe sterilized, and preferably added an appropriate amount of sodium chloride, glucose or glycerol and so on, to prepare an injection which is isotonic compared with blood. In the preparation of injections, any common used carriers in the present field may be used. For example, water, ethanol, propylene glycol, the ethoxylated iso-stearyl alcohol, polyoxylated iso-stearyl alcohol and polyethylene dehydrated sorbitan fatty acid ester and so on. In addition, the usual solvent, buffer, and analgesics may be added. During the treatment of schizophrenia, coloring agents, preservatives, spices, flavoring agents, sweetening agents and other drugs may also be added based on the requirements.

The content of dithiolopyrrolone compounds shown as formula I in this invention or pharmaceutically acceptable salt thereof in the pharmaceutical composition is not specially restricted, and may be selected within a wide range, usually is 1~70% mass percent, preferably is 1~30% mass percent.

In the present invention, the administration of the pharmaceutical compositions described is not specially restricted. A variety of formulation administration may be selected according to the patient's age, gender and other conditions as well as symptoms. For example, tablets, pills, solution, suspension, emulsion, granules and capsules are oral administration; injection may be administered alone, or be intravenous injected with the mixture of transmission solution for injecting (eg glucose solution and amino acid solution), if necessary injection may be simply carried out through muscle, intradermal, subcutaneous, or intra-abdominal injection; suppository can be administered to the rectum.

In the present invention, dosage may be appropriately selected according to the administration method, patient's age, gender and other conditions as well as symptoms. The usual dosage may be administrated as follows: about 0.1~300 mg drug active ingredient/kg body weight/day. In general, each administration unit formulation may contain 1~200 mg drug active ingredient.

The invention further related to the application of the dithiolopyrrolone compounds in this invention and pharmaceutically acceptable salt thereof, in preparing medicaments for elevating peripheral white blood cells, as well as in the preparation of adjunctive medicaments in the radiotherapy or chemotherapy for inhibiting the reduction of peripheral white blood cells. In the invention, white blood cells described are preferably neutrophils. The compounds of this invention have a significant effect in promoting the maturation and differentiation of bone marrow, and promoting the peripheral leukocytosis rapidly and sustainedly, see the examples of the efficacy.

The reagents and raw materials in the invention are commercially available unless otherwise stated.

The advantage of invention is: the small molecule pharmaceutically active compounds dithiolopyrrolone of the invention and pharmaceutically acceptable salt thereof have a significant effect in promoting the maturation and differentiation of bone marrow, and promoting the peripheral leukocytosis rapidly and sustainedly, and the storage and transportation are convenient to avoid the shortcomings of existing protein peptide drugs including easy inactivation, shorter half-life, and the use of inconvenient, moreover, its preparation method is simple and has lower cost, so it's cheaper.

EXAMPLES

The following examples are illustrative for the present invention, but shouldn't be considered to limit the present invention in any way. The scope of the invention is limited by the subsidiary claims.

The several preparation methods of the compounds of this invention are illustrated in the following programs and examples. Raw materials are commercially available or prepared according to the known literature methods or scheme as shown. It should be understood by those skilled in the art that the compounds of this invention may be synthesized by other synthetic routes. Although the specific materials and conditions of the synthetic route has been illustrated below, they may be easily replaced with other similar materials and conditions, the deformation of these preparation methods of this invention are included in the scope of the present invention. In addition, the preparation method described below may be further modified with the conventional chemical methods with which those skilled in the art was familiar in this field, according to the disclosed content of the present invention, for example, appropriate groups are protected during the reaction and so on.

The following examples are used to promote the further understanding of the preparation method of the present invention. The specific materials used, types and conditions are identified as a further explanation of this invention, but not limit its reasonable range. The reagents used in the synthesis of compounds showed in the following table are commercially available or prepared easily by those skilled in the art. The operating conditions of $^1$H-NMR are as follows: $^1$H-NMR is determined on the INOVA-400 NMR instrument with TMS as internal standard. MS is obtained on the HP5989A mass spectrometer.

The Preparation of Compound I-6

The preparation of 1,3-ditert-mercapto acetone (I-1)

To a solution of tert-butyl mercaptan (95.0 g, 1.1 mol), anhydrous potassium carbonate (304.0 g, 2.2 mol) and acetone (1 L), in 2 L four-neck reaction flask at 10° C., was added dropwise an equivalent 1,3-dichloro-acetone (63.5 g, 0.5 mol) in acetone solution with the rate of dropwise at 5 ml/min. After the addition, the solution was stirred at room temperature overnight. The precipitate was filtered and washed with acetone (100 ml×2), and the filtrate was evaporated under reduced pressure to remove solvents. The residue was distilled in vacuum, 110° C. (8 mm) fraction was collected to give pale yellow oil of I-1 (107.6 g, 92.1%).

Preparation of 4-tertbutyl mercapto-5-tertbutyl mercapto methenyl-1-(2,4-dimethoxy-phenyl)-3-hydroxy-1,5-dihydropyrrolidone (I-2)

2,4-dimethoxy-aniline (68.9 g, 0.45 mol), compound I-1 (105.8 g, 0.45 mol), p-toluenesulfonic acid (8.6 g, 0.05 mol), and toluene (1.2 L) was added in 2 L four-neck reaction flask with water segregator device. The reaction solution was refluxed and removed water for 8 h, and then cooled and maintained at −10° C., added dropwise oxalyl chloride (57.2 g, 0.45 mol), after addition, continue to stir for 2 h, added dropwise triethylamine (91 g, 0.9 mol), after addition, naturally warmed to room temperature and stirred overnight. Toluene was evaporated in vacuum, and the residue was added methylene chloride (500 ml), washed with water (300 ml×3). The organic phase was dried with anhydrous sodium sulfate, filtered. The solvent was evaporated in vacuum, and the residue was recrystallized with isopropyl alcohol, to give pale yellow solid of I-2 (128 g, 67.4%), melting point 165° C.-167° C.

Preparation of 4-tertbutyl mercapto-5-tertbutyl mercapto methenyl-1-(2,4-dimethoxy-phenyl)-3-amino-1,5-dihydropyrrolidone (I-3)

To the solution of compound I-2 (10.2 g, 0.24 mol), butyric acid (140 ml), and toluene (20 ml) in 250 ml four-neck reaction flask with water segregator device, was led ammonia to saturation. The reaction solution was refluxed and removed water for 6 h, constantly led into the ammonia, after the reaction was completed, the mixture was poured into 2M sodium hydroxide solution (450 ml) at 0° C., extracted with ethyl acetate (200 ml×2). The organic phase was washed with water (300 ml×2), dried with anhydrous sodium sulfate, filtered. The solvent was evaporated in vacuum, and the residue was recrystallized with ethyl acetate/petroleum ether, to give pale solid of I-3 (5.2 g, 50%), melting point 140° C.-143° C.

Preparation of 4-tertbutyl mercapto-5-tertbutyl mercapto methenyl-1-(2,4-dimethoxy-phenyl)-3-trifluoro acetamido-1,5-dihydropyrrolidone (I-4)

To a solution of compound I-3 (5 g, 11.8 mmol) in dichloromethane (20 ml), was added dropwise trifluoroacetic anhydride (3.7 g, 17.8 mmol). The solution was stirred at room temperature for 30 min. The solvent was evaporated under reduced pressure. After adding n-hexane (50 ml), the precipaitate was filtered, dried to give yellow powdery solid of I-4 (5.8 g, 95%), melting point 180° C.-181° C.

Preparation of N-[4-(2,4-dimethoxyphenyl)-5-oxo-4,5-dihydro-[1,2]dithioleheterocyclicpentene[4,3-b]pyrrolyl]-2,2,2-trifluoroacetamide (I-5)

To a solution of compound I-4 (5.8 g, 11.2 mmol) in trifluoroacetic acid (20 ml), was added mercury acetate (3.2 g, 11.2 mmol). The solution was stirred at room temperature for 30 min. The solvent was evaporated under reduced pressure. After adding ethanol (20 ml), the precipaitate was filtered, dried to give yellow solid (6.4 g, 95%), its melting point is more than 270° C.

To the solution of the above compound (6.4 g, 10.8 mmol), acetonitrile (100 ml) in 150 ml four-neck reaction flask at room temperature, was led hydrogen sulfide gas until the system no longer absorbed hydrogen sulfide. The reaction solution was led nitrogen to blow away the residual hydrogen sulfide gas, added iodine (2.7 g, 10.8 mmol) in dichloromethane (20 ml) solution, continually stirred for 1 h. The solvent was evaporated under reduced pressure. After adding methanol (20 ml), the precipaitate was filtered, dried to give yellow solid I-5 (0.8 g, 20%), melting point 188° C.-190° C.

Preparation of 6-amino-4-(2,4-dimethoxyphenyl)-4H-[1,2]dithioleheterocyclicpentene[4,3-b]-5-pyrrolone hydrochloride (I-6)

Compound I-5 (1.9 g, 4.7 mmol), methanol (20 ml), and concentrated hydrochloric acid (5 ml) was added into a 50 ml single neck bottle. The solution was heated to reflux for 3 h, and filtered while hot to remove the insoluble materials. The filtrate was stirred overnight at room temperature, filtered, dried to give solid of I-6 (1.3 g, 80%), melting point 230° C.-232° C.

Preparation method of 6-amino-4-(2-methylphenyl)-4H-[1,2]dithioleheterocyclicpentene[4,3-b]-5-pyrrolone hydrochloride (I-6) is the same as the method described above.

$^1$H-NMR (DMSO-d6): 2.16 (3H, s), 4.41 (2H, s), 6.56 (1H, s), 7.19-7.37 (4H, m)

m/z: 262.02

Preparation of Compounds Shown as Formula I in the Invention

Table 1 shows a series of compounds shown as formula I 001~033, obtained from the 6-Amino-4-(2,4-dimethoxyphenyl)-4H-[1,2]dithioleheterocyclicpentene[4,3-b]-5-pyrrolone (I-6) which is prepared by the above methods, according to the preparation method of the present invention.

TABLE 1

Dithiolopyrolone compounds of the present invention

| No. | X | $R_1$ | $R_2$ | $R_3$ | $R_4$ |
|-----|---|-------|-------|-------|-------|
| 001 | O | 2,4-dimethoxyphenyl | H | phenyl | \ |
| 002 | O | 2,4-dimethoxyphenyl | H | 2-methylpropyl | \ |
| 003 | O | 2,4-dimethoxyphenyl | H | benzyl | \ |
| 004 | O | 2,4-dimethoxyphenyl | H | ethyl | \ |
| 005 | O | 2,4-dimethoxyphenyl | H | methyl | \ |
| 006 | O | 2,4-dimethoxyphenyl | H | H | \ |
| 007 | O | 2,4-dimethoxyphenyl | H | isopropyl | \ |
| 008 | O | 2,4-dimethoxyphenyl | H | allyl | \ |
| 009 | O | 2,4-dimethoxyphenyl | H | propyl | \ |
| 010 | O | 2,4-dimethoxyphenyl | H | 4-methoxyphenyl | \ |
| 011 | O | 2,4-dimethoxyphenyl | H | amyl | \ |
| 012 | O | 2,4-dimethoxyphenyl | H | pyranylmethyl | \ |
| 013 | O | 2,4-dimethoxyphenyl | H | butyl | \ |
| 014 | O | 2,4-dimethoxyphenyl | H | cyclopentyl | \ |
| 015 | O | 2,4-dimethoxyphenyl | H | heptyl | \ |
| 016 | O | 2,4-dimethoxyphenyl | H | 2-chloro-ethyl | \ |
| 017 | O | 2,4-dimethoxyphenyl | H | 4-chlorophenyl | \ |
| 018 | O | 2,4-dimethoxyphenyl | H | 4-methyl-phenyl | \ |
| 019 | O | 2,4-dimethoxyphenyl | H | 2-furan methyl | \ |
| 020 | O | 2,4-dimethoxyphenyl | H | 1-phenylethyl | \ |
| 021 | O | 2,4-dimethoxyphenyl | H | 2-thiophene methyl | \ |
| 022 | O | 2,4-dimethoxyphenyl | H | 3-pyridyl | \ |
| 023 | $NR_4$ | 2,4-dimethoxyphenyl | H | N,N-diethoxy | H |
| 024 | $NR_4$ | 2,4-dimethoxyphenyl | H | benzyl | H |
| 025 | $NR_4$ | 2,4-dimethoxyphenyl | H | butyl | H |
| 026 | $NR_4$ | 2,4-dimethoxyphenyl | H | phenyl | H |
| 027 | S | 2,4-dimethoxyphenyl | H | ethyl | \ |
| 028 | O | 2-methylphenyl | H | ethyl | \ |
| 029 | O | 2-methylphenyl | H | phenyl | \ |
| 030 | O | 2-methylphenyl | H | allyl | \ |
| 031 | O | 2,4-dimethoxyphenyl | H | N,N-dimethylaminoethyl | \ |

Preparation of 001

To a solution of the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol) and triethylamine (200 mg, 2 mmol) in tetrahydrofuran (20 ml) at −20° C., was added dropwise phenyl chloroformate (281 mg, 1.8 mmol). The solution was stirred for 5 h. The solvent was evaporated under reduced pressure, and the residue was added methylene chloride (20 ml), washed with water (20 ml×3). The organic phase was dried with anhydrous sodium sulfate, and the solvent was evaporated in vacuum. The obtained solid was purified by column chromatography with chloroform/methanol to give 001 (273 mg).

m.p 204° C.-206° C.

$^1$H-NMR (DMSO-d6): 3.75 (3H, s), 3.84 (3H, s), 6.63-6.83 (3H, m), 7.20-7.46 (6H, m), 10.10 (1H, s)

m/z: 428.05

Preparation of 002

To a solution of the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol) and triethylamine (300 mg, 3 mmol) in tetrahydrofuran (20 ml) at 0° C., was added dropwise isobutyl chloroformate (1.2 g, 2.7 mmol). The solution was stiffed for 1.5 h. The solvent was evaporated under reduced pressure, and the residue was added methylene chloride (20 ml), washed with water (20 ml×3). The organic phase was dried with anhydrous sodium sulfate, and the solvent was evaporated in vacuum. The obtained solid was purified by column chromatography with chloroform/methanol to give 002 (248 mg).

m.p 226° C.-227° C.
$^1$H-NMR (DMSO-d6): 0.92 (6H, d), 1.91 (1H, m), 3.74 (3H, s), 3.82 (3H, s), 3.89 (2H, d), 6.60-6.75 (3H, m), 7.19 (1H, d), 9.35 (1H, s)
m/z: 408.08

Preparation of 003

To a solution of the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol) and triethylamine (181 mg, 1.8 mmol) in tetrahydrofuran (20 ml) at 20° C., was added dropwise benzyl chloroformate (1.53 g, 4.5 mmol). The solution was stirred for 1 h. The solvent was evaporated under reduced pressure, and the residue was added methylene chloride (20 ml), washed with water (20 ml×3). The organic phase was dried with anhydrous sodium sulfate, and the solvent was evaporated in vacuum. The obtained solid was purified by column chromatography with chloroform/methanol to give 003 (260 mg).

m.p 165° C.-166° C.
$^1$H-NMR (DMSO-d6): 3.74 (3H, s), 3.82 (3H, s), 3.89 (2H, s) 6.60-6.75 (3H, m), 7.10-7.90 (6H, m), 9.35 (1H, s)
m/z: 442.07

Preparation of 004

To a solution of the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol) and triethylamine (181 mg, 1.8 mmol) in tetrahydrofuran (20 ml) at 50° C., was added dropwise ethyl chloroformate (97 mg, 0.9 mmol). The solution was stirred for 1 h. The solvent was evaporated under reduced pressure, and the residue was added methylene chloride (20 ml), washed with water (20 ml×3). The organic phase was dried with anhydrous sodium sulfate, and the solvent was evaporated in vacuum. The obtained solid was purified by column chromatography with chloroform/methanol to give 004 (228 mg).

m.p 208° C.-210° C.
$^1$H-NMR (DMSO-d6): 1.25 (3H, m), 3.74 (3H, s), 3.84 (3H, s), 4.17 (2H, m), 6.62-6.76 (3H, m), 7.72 (1H, d), 9.31 (1H, s)
m/z: 380.05

Preparation of 005

To a solution of the intermediate 6-amino-4-(2,4-dimethoxyphenyl)-4H-[1,2]dithioleheterocyclicpentene[4,3-b]-5-pyrrolone hydrochloride (I-6) (500 mg, 1.5 mmol) and triethylamine (272 mg, 2.7 mmol) in tetrahydrofuran (30 ml) at 30° C., was added dropwise methyl chloroformate (1.42 g, 15 mmol). The solution was stirred for 30 min. The solvent was evaporated under reduced pressure, and the residue was added methylene chloride (30 ml), washed with water (20 ml×3). The organic phase was dried with anhydrous sodium sulfate, and the solvent was evaporated in vacuum. The obtained solid was purified by column chromatography with chloroform/methanol to give 005 (380 mg).

m.p 186° C.-188° C.
$^1$H-NMR (DMSO-d6): 3.68 (3H, s), 3.72 (3H, s), 5.82 (3H, s), 6.37-6.80 (3H, m), 7.23 (1H, d), 9.4 (1H, s)
m/z: 366.03

Preparation of 006

To a solution of the intermediate 6-amino-4-(2,4-dimethoxyphenyl)-4H-[1,2]dithioleheterocyclicpentene[4,3-b]-5-pyrrolone hydrochloride (I-6) (400 mg, 1.2 mmol) and triphosgene (234 mg, 0.8 mmol) in tetrahydrofuran (20 ml) at room temperature, was added dropwise triethylamine (272 mg, 2.7 mmol). The solution was stirred for 1 h. The 80% solvent was evaporated under reduced pressure, added concentrated hydrochloric acid (1 ml), stirred for 5 min, the resulted mixture was evaporated in vacuum to remove the remaining solvent, and the residue was added methylene chloride (20 ml), washed with water (20 ml×3). The organic phase was dried with anhydrous sodium sulfate, and the solvent was evaporated in vacuum. The obtained solid was purified by column chromatography with chloroform/methanol to give 006 (240 mg).

m.p 245° C.-248° C.
$^1$H-NMR (DMSO-d6): 3.73 (3H, s), 3.82 (3H, s) 6.22-6.73 (4H, m), 7.18 (1H, d), 8.31 (1H, s)
m/z: 351.03

Preparation of 007

To a solution of isopropanol (36 mg, 0.6 mmol), triethylamine (61 mg, 0.6 mmol) in dichloromethane (20 ml) at 0° C., was added dropwise triphosgene (180 mg, 0.6 mmol) in dichloromethane (5 ml). The solution was naturally warmed to room temperature, stirred for 30 min, washed with water (20 ml×3). The organic phase was dried with anhydrous sodium sulfate, and the solvent was evaporated in vacuum. The residue was added dichloromethane (20 ml) and the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 2 h at room temperature, washed with water (20 ml×3). The organic phase was dried with anhydrous sodium sulfate, and the solvent was evaporated in vacuum. The obtained solid was purified by column chromatography with chloroform/methanol to give 007 (260 mg).

m.p 230° C.-232° C.
$^1$H-NMR (DMSO-d6): 1.24 (6H, d), 3.72 (3H, s), 3.81 (3H, s), 4.87 (1H, s), 6.59-7.18 (4H, m), 9.14 (1H, s)
m/z: 394.09

Preparation of 008

To a solution of the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol) and triethylamine (181 mg, 1.8 mmol) in chloroform (20 ml) at room temperature, was added dropwise allyl chloroformate (216 mg, 1.8 mmol). The solution was stirred for 1.5 h, washed with water (20 ml×3). The organic phase was dried with anhydrous sodium sulfate, and the solvent was evaporated in vacuum. The obtained solid was purified by column chromatography with chloroform/methanol to give 008 (290 mg).

m.p 210° C.-212° C.

$^1$H-NMR (DMSO-d6): 3.73 (3H, s), 3.81 (3H, s), 4.61 (2H, d), 5.23 (1H, dd), 5.39 (1H, dd), 5.95 (2H, m), 6.60-7.19 (4H, m), 9.48 (1H, s)

m/z: 392.06

Preparation of 009

To a solution of propanol (36 mg, 0.6 mmol), triethylamine (61 mg, 0.6 mmol) in tetrahydrofuran (20 ml) at 0° C., was added dropwise triphosgene (180 mg, 0.6 mmol) in tetrahydrofuran (5 ml). The solution was naturally warmed to room temperature, stirred for 30 min, then added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), the resulted mixture was stirred for 1.5 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 009 (285 mg).

m.p 202° C.-204° C.

$^1$H-NMR (DMSO-d6): 0.96 (3H, t), 1.61 (2H, m), 3.18 (2H, t), 3.78 (3H. s), 3.84 (3H, s), 6.28-7.50 (4H. m), 9.31 (1H. s)

m/z: 394.06

Preparation of 010

To a solution of 4-methoxyphenol (74.4 mg, 0.6 mmol), triethylamine (61 mg, 0.6 mmol) in tetrahydrofuran (20 ml) at 0° C., was added dropwise triphosgene (180 mg, 0.6 mmol) in tetrahydrofuran (5 ml). After addition, the solution was stirred for 1.5 h at 40° C., added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), the resulted mixture was stirred for 3.5 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 010 (180 mg).

m.p 204° C.-207° C.

$^1$H-NMR (DMSO-d6): 3.73 (3H, s), 3.74 (3H, s), 3.83 (3H, s), 6.62-7.23 (8H, m), 9.99 (1H, s)

m/z: 458.06

Preparation of 011

To a solution of pentanol (53 mg, 0.6 mmol), triethylamine (61 mg, 0.6 mmol) in tetrahydrofuran (20 ml) at 0° C., was added dropwise triphosgene (180 mg, 0.6 mmol) in tetrahydrofuran (5 ml). The solution was naturally warmed to room temperature, stirred for 1 h, added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), the resulted mixture was stirred for 2.5 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 011 (240 mg).

m.p 178° C.-179° C.

$^1$H-NMR (DMSO-d6): 0.89 (3H, t), 1.34 (4H, m), 1.61 (2H, t), 3.74 (3H, s), 3.83 (3H, s), 4.09 (2H, t), 6.61-7.21 (4H, m), 9.33 (1H, s)

m/z: 422.10

Preparation of 012

To a solution of tetrahydrofurfuryl alcohol (61 mg, 0.6 mmol), triethylamine (61 mg, 0.6 mmol) in tetrahydrofuran (20 ml) at 0° C., was added dropwise triphosgene (180 mg, 0.6 mmol) in tetrahydrofuran (5 ml). The solution was naturally warmed to room temperature, stirred for 30 min, added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 2 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 012 (243 mg).

m.p 156° C.-158° C.

$^1$H-NMR (DMSO-d6): 1.95 (4H, m), 3.77 (3H, s), 3.87 (3H, s), 3.91 (1H, m), 3.93 (2H, d), 4.25 (2H, t), 6.28-6.58 (3H, m), 6.97 (1H, s), 7.18 (1H, d)

m/z: 436.08

Preparation of 013

To a solution of butanol (44 mg, 0.6 mmol), triethylamine (61 mg, 0.6 mmol) in tetrahydrofuran (20 ml) at 0° C., was added dropwise triphosgene (180 mg, 0.6 mmol) in tetrahydrofuran (5 ml). The solution was naturally warmed to room temperature, stirred for 1 h, added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 2 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 013 (280 mg).

m.p 177° C.-178° C.

$^1$H-NMR (DMSO-d6): 0.91 (3H, t), 1.38 (2H, m), 1.59 (2H, m), 3.73 (3H, s), 3.82 (3H, s), 4.11 (2H, t), 6.61-7.20 (4H, m), 9.31 (1H, s)

m/z: 408.08

Preparation of 014

To a solution of cyclopentanol (78 mg, 0.9 mmol), triethylamine (90 mg, 0.9 mmol) in tetrahydrofuran (20 ml) at 0° C., was added dropwise triphosgene (270 mg, 0.9 mmol) in tetrahydrofuran (5 ml). The solution was naturally warmed to room temperature, stirred for 1.5 h, added the intermediate 6-amino-4-(2,4-dimethoxyphenyl)-4H-[1,2]dithioleheterocyclicpentene[4,3-b]-5-pyrrolone hydrochloride (I-6) (500 mg, 1.5 mmol), stirred for 3 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 014 (300 mg).

m.p 228° C.-230° C.
$^1$H-NMR (DMSO-d6): 1.56 (2H, s), 1.69 (2H, s), 1.85 (2H, t), 3.72 (3H, s), 3.82 (3H, s), 5.07 (1H, s), 6.61-7.19 (4H, m), 9.16 (1H, s)
m/z: 420.08

Preparation of 015

To a solution of heptanol (70 mg, 0.6 mmol), triethylamine (61 mg, 0.6 mmol) in tetrahydrofuran (20 ml) at 0° C., was added dropwise triphosgene (180 mg, 0.6 mmol) intetrahydrofuran (5 ml). The solution was naturally warmed to room temperature, stirred for 1.5 h, added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 2 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 015 (220 mg).

m.p 144° C.-146° C.
$^1$H-NMR (DMSO-d6): 0.87 (3H, t), 1.31 (8H, t), 1.59 (2H, t), 3.72 (3H, s), 3.82 (3H, s), 4.09 (2H, t), 6.61-7.20 (4H, m), 9.31 (1H, s)
m/z: 450.13

Preparation of 016

To a solution of chloroethanol (48 mg, 0.6 mmol), triethylamine (61 mg, 0.6 mmol) in tetrahydrofuran (20 ml) at 0° C., was added dropwise triphosgene (180 mg, 0.6 mmol) in tetrahydrofuran (5 ml). The solution was naturally warmed to room temperature, stirred for 30 min, added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 1 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 016 (260 mg).

m.p 211° C.-214° C.
$^1$H-NMR (DMSO-d6): 3.72 (3H, s), 3.82 (3H, s), 4.37 (2H, t), 6.61-7.21 (4H, m), 9.61 (1H, s)
m/z: 414.01

Preparation of 017

To a solution of 4-chlorophenol (77 mg, 0.6 mmol), triethylamine (61 mg, 0.6 mmol) in tetrahydrofuran (20 ml) at 0° C., was added dropwise triphosgene (180 mg, 0.6 mmol) in tetrahydrofuran (5 ml). After addition, the solution was stirred for 1.5 h at 40° C., added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 3.5 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 017 (200 mg).

m.p 233° C.-236° C.
$^1$H-NMR (DMSO-d6): 3.75 (3H, s), 3.84 (3H, s), 6.48-7.70 (8H, m), 9.53 (1H, s)
m/z: 462.01

Preparation of 018

To a solution of 4-methylphenol (65 mg, 0.6 mmol), triethylamine (61 mg, 0.6 mmol) in tetrahydrofuran (20 ml) at 0° C., was added dropwise triphosgene (180 mg, 0.6 mmol) in tetrahydrofuran (5 ml). After addition, the solution was stirred for 1 h at 40° C., added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 2 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 018 (210 mg).

m.p 260° C.-262° C.
$^1$H-NMR (DMSO-d6): 2.20 (3H, s), 3.75 (3H, s), 3.84 (3H, s), 6.61-7.77 (8H, m), 9.43 (1H, s)
m/z: 442.04

Preparation of 019

To a solution of 2-furan methanol (59 mg, 0.6 mmol), pyridine (56 mg, 0.7 mmol) in tetrahydrofuran (20 ml) at 0° C., was added dropwise triphosgene (180 mg, 0.6 mmol) in tetrahydrofuran (5 ml). The solution was naturally warmed to room temperature, stirred for 30 min, added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 1 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 019 (235 mg).

m.p 190° C.-191° C.
$^1$H-NMR (DMSO-d6): 3.73 (3H, s), 3.83 (3H, s), 5.14 (2H, s), 6.47-7.68 (7H, m), 9.52 (1H, s)
m/z: 432.01

Preparation of 020

To a solution of α-phenylethanol (73 mg, 0.6 mmol), triethylamine (61 mg, 0.6 mmol) in tetrahydrofuran (20 ml) at 0° C., was added dropwise triphosgene (180 mg, 0.6 mmol) in tetrahydrofuran (5 ml). The solution was naturally warmed to room temperature, stirred for 1.5 h, added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 1 h at 50° C., evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 020 (200 mg).

m.p 200° C.-203° C.
$^1$H-NMR (DMSO-d6): 2.94 (2H, t), 3.73 (3H, s), 3.83 (3H, s), 4.30 (2H, t), 6.61-7.31 (9H, m), 9.41 (1H, s)
m/z: 456.08

Preparation of 021

To a solution of 2-thiophene methanol (68 mg, 0.6 mmol), triethylamine (61 mg, 0.6 mmol) in tetrahydrofuran (20 ml) at −20° C., was added dropwise triphosgene (180 mg, 0.6 mmol) in tetrahydrofuran (5 ml). The solution was naturally warmed to room temperature, stirred for 1 h, added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 1 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 021 (225 mg).

m.p 225° C.-226° C.
$^1$H-NMR (DMSO-d6): 3.73 (3H, s), 3.82 (3H, s), 5.34 (2H, s), 6.61-7.57 (7H, m), 9.56 (1H, s)
m/z: 448.01

Preparation of 022

To a solution of 3-hydroxyl-pyridine (114 mg, 1.2 mmol), triethylamine (120 mg, 1.2 mmol) in tetrahydrofuran (30 ml) at −15° C., was added dropwise triphosgene (360 mg, 1.2 mmol) in tetrahydrofuran (5 ml). After addition, the solution was stirred for 1.5 h at 40° C., added the intermediate 6-amino-4-(2,4-dimethoxyphenyl)-4H-[1,2]dithioleheterocyclicpentene[4,3-b]-5-pyrrolone hydrochloride (I-6) (600 mg, 1.8 mmol), stirred for 3 h at 50° C., detected by TLC to indicate the completing of reaction, evaporated in vacuum to remove the remaining solvent, added dichloromethane (40 ml), washed with water (20 ml×3). The organic phase was dried with anhydrous sodium sulfate, and the solvent was evaporated in vacuum. The obtained solid was purified by column chromatography with chloroform/methanol to give 022 (300 mg).

m.p 176° C.-178° C.
$^1$H-NMR (DMSO-d6): 3.73 (3H, s), 3.82 (3H, s), 6.23-7.42 (8H, m), 10.23 (1H, s)
m/z: 429.05

Preparation of 023

To a solution of morpholine (52 mg, 0.6 mmol), triethylamine (61 mg, 0.6 mmol) in tetrahydrofuran (20 ml) at 0° C., was added dropwise triphosgene (180 mg, 0.6 mmol) intetrahydrofuran (5 ml). The solution was naturally warmed to room temperature, stirred for 1 h, added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stirred for 1 h at room temperature, detected by TLC to indicate the complete of reaction, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 023 (238 mg).

m.p 226° C.-227° C.
$^1$H-NMR (DMSO-d6): 3.43 (4H, t), 3.58 (4H, t), 3.72 (3H, s), 3.82 (3H, s), 6.60-7.20 (4H, m), 8.23 (1H, s)
m/z: 421.08

Preparation of 024

To tetrahydrofuran (10 ml) at −20° C., was led phosgene (88.2 mg, 0.9 mmol), added dropwise the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), and triethylamine (20 mg, 2 mmol) in tetrahydrofuran (20 ml). The solution was stirred for 1 h at −20° C., added benzylamine (94.5 mg, 0.9 mmol), stirred for 6 h at −20° C., detected by TLC to indicate the complete of reaction, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 024 (320 mg).

m.p 249° C.-250° C.
$^1$H-NMR (DMSO-d6): 3.72 (3H, s), 3.82 (3H, s), 4.31 (2H, s), 6.61-7.37 (9H, m), 8.39 (1H, s)
m/z: 441.08

Preparation of 025

To a solution of triphosgene (1.35 g, 4.5 mmol) in tetrahydrofuran (10 ml) at 0° C., was added dropwise the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), triethylamine (200 mg, 2 mmol) in tetrahydrofuran (20 ml). The solution was naturally warmed to room temperature, stirred for 1 h, added butylamine (0.56 g, 9 mmol), stirred for 2 h at room temperature, detected by TLC to indicate the complete of reaction, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 025 (270 mg).

m.p 247° C.-249° C.
$^1$H-NMR (DMSO-d6): 0.91 (3H, t), 1.38 (4H, m), 3.08 (2H, t), 3.74 (3H, s), 3.83 (3H, s), 6.61-7.21 (4H, m), 8.22 (1H, s)
m/z: 407.10

Preparation of 026

To a solution of triphosgene (2.7 g, 9 mmol) in tetrahydrofuran (10 ml) at 0° C., was added dropwise the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), pyridine (160 mg, 2 mmol) in tetrahydrofuran (20 ml). The solution was warmed to 50° C., stirred for 1 h, added aniline (418 mg, 4.5 mmol), stirred for 1 h at 50° C., evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 026 (300 mg).

m.p 220° C.-222° C.
$^1$H-NMR (DMSO-d6): 3.74 (3H, s), 3.83 (3H, s), 6.70-7.50 (9H, m), 8.58 (1H, s), 9.18 (1H, s)
m/z: 427.10

Preparation of 027

To a solution of ethanethiol (37 mg, 0.6 mmol), triethylamine (61 mg, 0.6 mmol) in tetrahydrofuran (20 ml) at 0° C., was added dropwise triphosgene (180 mg, 0.6 mmol) in tetrahydrofuran (5 ml). The solution was naturally warmed to room temperature, stirred for 30 min, added the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), stiffed for 1 h at 50° C., evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 027 (220 mg).

m.p 200° C.-202° C.
$^1$H-NMR (DMSO-d6): 1.23 (3H, t), 2.87 (2H, m), 3.74 (3H, s), 3.84 (3H, s), 6.62-7.72 (4H, m), 10.39 (1H, s)
m/z: 396.01

Preparation of 028

To a solution of the intermediate 6-amino-4-(2-methylphenyl)-4H-[1,2]dithioleheterocyclicpentene[4,3-b]-5-pyrrolone hydrochloride (I-6) (300 mg, 0.9 mmol) and triethylamine (181 mg, 1.8 mmol) in tetrahydrofuran (20 ml) at room temperature, was added dropwise ethyl chloroformate (194 mg, 1.8 mmol). The solution was stirred for 1 h at room temperature. The solvent was evaporated under reduced pressure, and the residue was added methylene chloride (20 ml), washed with water (20 ml×3). The organic phase was dried with anhydrous sodium sulfate, and the solvent was evaporated in vacuum. The obtained solid was purified by column chromatography with chloroform/methanol to give 028 (228 mg).

m.p 172° C.-174° C.
$^1$H-NMR (CDCl$_3$): 1.32 (3H, t), 2.15 (3H, s), 4.26 (2H, m), 6.30 (1H, s), 6.90 (1H, s), 7.20-7.35 (4H, m)
m/z: 334.04

Preparation of 029

To a solution of the intermediate 6-amino-4-(2-methylphenyl)-4H-[1,2]dithioleheterocyclicpentene[4,3-b]-5-pyrrolone hydrochloride (I-6) (300 mg, 0.9 mmol) and triethylamine (200 mg, 2 mmol) in tetrahydrofuran (20 ml) at room temperature, was added dropwise phenyl chloroformate (281 mg, 1.8 mmol). The solution was stiffed for 2 h at room temperature. The solvent was evaporated under reduced pressure, and the residue was added methylene chloride (20 ml), washed with water (20 ml×3). The organic phase was dried with anhydrous sodium sulfate, and the solvent was evaporated in vacuum. The obtained solid was purified by column chromatography with chloroform/methanol to give 029 (273 mg).

m.p 174° C.-176° C.
$^1$H-NMR (CDCl$_3$): 2.18 (3H, s), 6.36 (1H, s), 7.23 (1H, s), 7.19-7.40 (9H, m)
m/z: 382.04

Preparation of 030

To a solution of the intermediate 6-amino-4-(2-methylphenyl)-4H-[1,2]dithioleheterocyclicpentene[4,3-b]-5-pyrrolone hydrochloride (I-6) (300 mg, 0.9 mmol) and triethylamine (181 mg, 1.8 mmol) in chloroform (20 ml) at room temperature, was added dropwise allyl chloroformate (216 mg, 1.8 mmol). The solution was stiffed for 1.5 h at room temperature, washed with water (20 ml×3). The organic phase was dried with anhydrous sodium sulfate, and the solvent was evaporated in vacuum. The obtained solid was purified by column chromatography with chloroform/methanol to give 030 (290 mg).

$^1$H-NMR (CDCl$_3$): 2.17 (3H, s), 4.69 (2H, d), 5.32 (2H, m), 5.96 (1H, m), 6.32 (1H, s), 7.03 (1H, s), 7.19-7.34 (4H, m)
m/z: 346.04

Preparation of 031

To a solution of triphosgene (540 mg, 1.8 mmol) in tetrahydrofuran (10 ml) at 0° C., was added dropwise the intermediate 6-amino-4-(2,4-dimethoxyphenyl)-4H-[1,2]dithioleheterocyclicpentene[4,3-b]-5-pyrrolone hydrochloride (I-6) (300 mg, 0.9 mmol), triethylamine (200 mg, 2 mmol) in tetrahydrofuran (20 ml). The solution was naturally warmed to room temperature, stirred for 1 h, added N,N-dimethylaminoethanol (176 mg, 2.8 mmol), stirred for 3 h at room temperature, evaporated in vacuum to remove the remaining solvent, added dichloromethane (20 ml), washed with water (20 ml×3). The organic phase was dried with anhydrous sodium sulfate, and the solvent was evaporated in vacuum. The obtained solid was purified by column chromatography with chloroform/methanol to give 031 (270 mg). Product (200 mg) was added ethanol (20 ml), led dry HCl gas to make the solution's pH=2, evaporated in vacuum to remove the remaining solvent, to give hydrochloride of 031.

$^1$H-NMR (CDCl$_3$): 2.34 (6H, s), 2.71 (2H, t), 3.72 (3H, s), 3.82 (3H, s), 4.23 (2H, t), 6.58 (1H, s), 6.74-7.20 (3H, m)
m/z: 423.05

Examples Of Oral Formulation

| Prescription 1: | 002 | 5 mg |
|---|---|---|
| | Cross-linked sodium carboxymethyl cellulose | 10 mg |
| | Starch | 20 mg |
| | Mannitol | 80 mg |
| | Sodium lauryl sulfate | 4 mg |
| | 30% ethanol (1.4% Tween 80) | appropriate |
| | Magnesium stearate | 1 mg |
| Prescription 2: | 004 | 5 mg |
| | Sodium carboxymethyl cellulose | 15 mg |
| | Starch | 20 mg |
| | Lactose | 75 mg |
| | Sodium lauryl sulfate | 5 mg |
| | 40% ethanol | appropriate |
| | Magnesium stearate | 1 mg |
| Prescription 3: | 005 | 5 mg |
| | Dextrin | 22 mg |
| | Lactose | 80 mg |
| | Sodium lauryl sulfate | 7 mg |
| | 50% ethanol | appropriate |
| | Magnesium stearate | 1 mg |
| Prescription 4: | 008 | 5 mg |
| | hydroxypropyl methyl cellulose( | 15 mg |
| | Lactose | 85 mg |
| | Sodium lauryl sulfate | 7 mg |
| | 30% ethanol (1% Tween 80) | appropriate |
| | Magnesium stearate | 1 mg |

According to the above formula, capsules or tablets etc. can be prepared by conventional methods.

Example 1 of Efficacy

Effects of Dithiolopyrrolone Series of Compounds on Peripheral Blood Leukocytes of Normal Mice 1. Experimental Samples and Equipments
Sample: dithiolopyrrolone series of compounds were dissolved in 0.5% CMC—Na to be suspension after grinding with Tween (less than 4% usage).

SAIGELI (G-CSF), Shanghai Sunway Biotech Co., Ltd., batch number: 051001

Animal hematology analyzer, model: HEMAVET950

2. Method

The mice were divided into blank control group, positive control group and the dithiolopyrrolone series of compounds group, there are 10 mice in each group. Positive control group was injected SAIGELI (G-CSF) (22.5 ug/kg) subcutaneously once a day; the mice in dithiolopyrrolone series of compounds group were administered ig (20 mg/kg), through gavaging once a day (0.5 ml); blank control group mice were administered ig an equivalent 0.5% CMC—Na solution.

Blood specimens were collected according to conventional method via the mice orbital vein, on the third, fifth day before and after administration respectively, the peripheral blood routine test was carried out, and the effect of dithiolopyrrolone series of compounds on peripheral blood leukocytes of normal mice was analyzed.

3. Results

TABLE 3

Effects of series of dithiolopyrrolone compounds on peripheral blood leukocytes of normal mice (WBC count × $10^9$/L)

| | Group/number of days | | | | | |
|---|---|---|---|---|---|---|
| | 0 | | 3 | | 5 | |
| | WBC | NE % | WBC | NE % | WBC | NE % |
| 001 | 7.89 | 33.73 | 18.24 | 67.44 | 24.96 | 72.13 |
| 002 | 8.12 | 20.11 | 11.89 | 52.13 | 16.78 | 68.69 |
| 003 | 7.84 | 32.51 | 14.56 | 54.34 | 17.44 | 68.30 |
| 004 | 7.65 | 31.56 | 13.36 | 56.36 | 18.66 | 78.24 |
| 005 | 8.08 | 26.46 | 8.76 | 35.55 | 8.64 | 46.65 |
| 006 | 7.8 | 19.86 | 12.54 | 56.13 | 13.11 | 62.43 |
| 007 | 8.11 | 23.31 | 11.88 | 48.67 | 12.22 | 52.02 |
| 008 | 8.88 | 31.56 | 17.79 | 60.03 | 18.76 | 65.55 |
| 009 | 9.01 | 23.62 | 13.9 | 27.46 | 14.21 | 47.78 |
| 010 | 8.87 | 20.86 | 10.18 | 24.34 | 10.23 | 32.34 |
| 011 | 8.76 | 27.68 | 11.46 | 46.65 | 11.88 | 51.87 |
| 012 | 9.03 | 34.02 | 11.46 | 38.98 | 12.01 | 49.07 |
| 013 | 6.36 | 25.6 | 12.69 | 48.76 | 13.29 | 52.84 |
| 014 | 6.78 | 20.81 | 11.56 | 23.39 | 12.01 | 40.40 |
| 015 | 7.46 | 20.76 | 11.56 | 25.65 | 13.34 | 38.87 |
| 016 | 7.34 | 18.79 | 10.47 | 40.47 | 11.56 | 45.76 |
| 017 | 6.36 | 23.24 | 8.67 | 28.88 | 8.88 | 36.90 |
| 018 | 6.15 | 21.74 | 8.59 | 23.38 | 9.03 | 26.04 |
| 019 | 6.88 | 24.36 | 9.35 | 28.89 | 10.87 | 29.84 |
| 020 | 5.09 | 30.03 | 9.61 | 38.66 | 11.22 | 42.49 |
| 021 | 5.22 | 29.78 | 9.93 | 36.52 | 11.22 | 49.65 |
| 022 | 6.86 | 31.23 | 10.03 | 38.98 | 12.11 | 47.74 |
| 023 | 7.86 | 26.86 | 22.34 | 56.66 | 29.98 | 77.31 |
| 024 | 7.95 | 24.67 | 8.76 | 33.98 | 9.71 | 42.02 |
| 026 | 7.84 | 28.98 | 8.76 | 30.38 | 9.71 | 38.63 |
| 027 | 8.76 | 24.45 | 11.22 | 45.46 | 12.54 | 48.37 |
| G-CSF | 6.74 | 25.39 | 17.48 | 57.86 | 19.22 | 60.68 |
| blank control | 8.04 | 21.74 | 8.36 | 26.46 | 8.24 | 35.87 |

Note:
WBC is white blood cell,
NE % is the percentage of neutrophils in the total number of white blood cells The results showed that these compounds had different degrees of efficacy of increasing peripheral blood leukocytes, but had no significant effect on red blood cells and platelets.

Example 2 of Efficacy

Effects of Series of Dithiolopyrrolone Compounds on Peripheral Blood Leukocytes of Normal Mice 1. Experimental Samples and Equipments Sample: series of dithiolopyrrolone compounds were dissolved in 0.5% CMC—Na to be suspension after grinding with Tween (less than 4% usage).

Cyclophosphamide for Injection (CTX), Shanghai Hualian Pharmaceutical Co., Ltd., batch number: 050606, prepared of being dissolved in saline.

SAIGELI (G-CSF), Shanghai Sunway Biotech Co., Ltd., batch number: 051001

Animal blood analyzer, model: HEMAVET950

2. Method

40 BALB/c mice, were randomly divided into five groups, blank control group, positive control (G-CSF) group (22.5 ug/kg), and two dithiolopyrrolone derivatives groups (compounds 001 and 004, 20 mg/kg), CTX model group (100 mg/kg), respectively with 8 mice in each group. rThe blank control group wasn't treated in any way, the other four groups were treated with CTX intraperitoneal injection, 100 mg/kg, once a day. After Continuous administration of three days, routine blood test of each group of mice were detected by Animal blood analyzer, and the results showed that the total number of white blood cells and the percentage of neutrophils were significantly decreased, suggesting that the model of CTX-induced hematopoietic dysfunction in mice was successfully created. G-CSF group was given G-CSF (22.5 ug/kg) subcutaneously once a day, one day after the completing of the injection of CTX. Dithiolopyrrolone derivatives groups were administered with dithiolopyrrolone derivatives (20 mg/kg), through gavaging once a day (0.5 ml), one day after the completing of the injection of CTX. The mice of model group and blank control group were administered with an equivalent 0.5% CMC—Na solution through gavaging.

Blood specimens were collected according to conventional method via the mice orbital vein, on the 0, 4, 6, 8 day respectively, when the day of administering CTX is set as the first day, then the peripheral blood routine test was carried out, and the effect of series of dithiolopyrrolone compounds on peripheral blood leukocytes of normal mice was analyzed.

3. Results

The leucocyte-stimulating activity was studied on compounds 001 and 004, regarding G-CSF as a control drug, and the results were shown in Table 4:

TABLE 4

Effects of series of dithiolopyrrolone compounds on peripheral blood leukocytes of model mice (WBC count × $10^9$/L)

| | Group/number of days | | | | | | | |
|---|---|---|---|---|---|---|---|---|
| | 0 | | 4 | | 6 | | 8 | |
| | WBC | NE % | WBC | NE % | WBC | NE % | WBC | NE % |
| 001 | 5.98 | 27.32 | 1.21 | 2.48 | 2.75 | 42.71 | 18.44 | 76.84 |
| 004 | 5.86 | 18.65 | 1.11 | 4.34 | 1.42 | 36.47 | 15.28 | 87.62 |
| CTX | 5.88 | 28.46 | 1.34 | 3.33 | 1.2 | 6.7 | 5.7 | 38.32 |
| G-CSF | 5.92 | 30.34 | 1.14 | 4.58 | 1.84 | 30.07 | 15.4 | 59.68 |
| Blank control | 6.04 | 26.78 | 6.23 | 32.04 | 6.41 | 28.65 | 6.32 | 34.74 |

Note:
WBC is white blood cell;
NE % is the percentage of neutrophils in the total number of white blood cells The data in Table 4 showed that these compounds in the present invention had significant efficacy on increasing peripheral blood leukocytes in chemotherapy-induced leukopenia, but had no significant effect on red blood cells and platelets.

The bone marrow of mice mentioned above was smeared, and microscopic examination showed granulocyte series in 001, 004, G-CSF group with significant hyperplasia and speeding up of the differentiation and maturation. Granulocyte series in CTX group were severely inhibited after administration, and there was no particular in the bone marrow smears of the blank control group.

What is claimed is:

1. Dithiolopyrrolone compounds (Formula I) or their pharmaceutical acceptable salts:

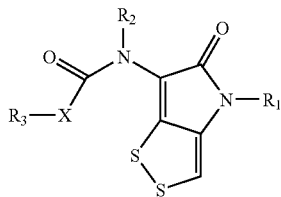

Wherein, X is O, NR$_4$ or S;

R$_1$ represents unsubstituted or optionally substituted following groups: C$_4$-C$_8$ cycloalkyl, C$_5$-C$_{10}$ aryl or three to ten-membered heterocyclic group having one to three heteroatoms independently selected from N, O or S;

R$_2$ represents hydrogen or C$_1$-C$_{10}$ alkyl;

R$_3$ represents hydrogen, or unsubstituted or optionally substituted following groups: C$_1$-C$_{10}$ alkyl, C$_2$-C$_{10}$ alkenyl, C$_2$-C$_{10}$ alkynyl, C$_3$-C$_{10}$ cycloalkyl, C$_1$-C$_{10}$ alkyl substituted by C$_5$-C$_{10}$ aryl, C$_5$-C$_{10}$ aryl, or three to ten-membered heterocyclic having one to three heteroatoms independently selected from N, O or S;

R$_4$ represents hydrogen or C$_1$-C$_{10}$ alkyl.

2. Dithiolopyrrolone compounds (Formula I) or their pharmaceutical acceptable salts according to claim 1, wherein the the substituted groups connected with the optionally substituted groups mentioned are selected from one or more of the following groups: C$_1$-C$_6$ alkyl, C$_1$-C$_6$ alkoxyl, C$_1$-C$_6$ alkylthio, halogen, C$_1$-C$_6$ alkoxycarbonyl, C$_1$-C$_6$ alkoxymethyl, aminomethyl, NH$_2$, NH(C$_1$-C$_6$ alkyl), N(C$_1$-C$_6$ alkyl)$_2$ and nitrogroup.

3. Dithiolopyrrolone compounds (Formula I) or their pharmaceutical acceptable salts according to claim 1, wherein R$_1$ is unsubstituted or optionally substituted following groups: C$_5$-C$_{10}$ aryl or five to ten-membered aromatic heterocyclic group having one to three heteroatoms independently selected from N, O or S.

4. Dithiolopyrrolone compounds (Formula I) or their pharmaceutical acceptable salts according to claim 3, wherein C$_5$-C$_{10}$ aryl is phenyl.

5. Dithiolopyrrolone compounds (Formula I) or their pharmaceutical acceptable salts according to claim 1, wherein R$_2$ is hydrogen.

6. Dithiolopyrrolone compounds (Formula I) or their pharmaceutical acceptable salts according to claim 1, wherein R$_3$ is unsubstituted or optionally substituted following groups: C$_1$-C$_{10}$ alkyl, C$_2$-C$_{10}$ alkenyl, C$_1$-C$_{10}$ alkyl with phenyl, phenyl, C$_3$-C$_{10}$ cycloalkyl or five to ten-membered aromatic heterocyclic group having one to three heteroatoms independently selected from N, O or S.

7. Dithiolopyrrolone compounds (Formula I) or their pharmaceutical acceptable salts according to claim 6, wherein R$_3$ is pyridyl, pyridazinyl, pyrimidinyl, C$_1$-C$_{10}$ alkyl with furyl, C$_1$-C$_{10}$ alkyl with thienyl, C$_1$-C$_6$ alkyl with pyrrolyl, or C$_1$-C$_{10}$ alkyl with pyranyl.

8. Dithiolopyrrolone compounds (Formula I) or their pharmaceutical acceptable salts according to claim 1, wherein the pharmaceutical acceptable salt is the salt from the reaction of dithiolopyrrolone compounds and pharmaceutical acceptable acid, or from the reaction of dithiolopyrrolone compounds having the acidic group and alkaline compounds.

9. Dithiolopyrrolone compounds (Formula I) or their pharmaceutical acceptable salts according to claim 8, wherein the acid is selected from inorganic acid, and organic acids; the alkaline compounds is selected from sodium hydroxide, potassium hydroxide, calcium hydroxide, sodium carbonate or potassium bicarbonate.

10. A process for preparing dithiolopyrrolone compounds (Formula I) or their pharmaceutically acceptable salts, including the following steps: the reaction is carried out between the compound shown as formula I-6 and chloroformate or chlorine formamide via organic base in the nonprotonic solvent,

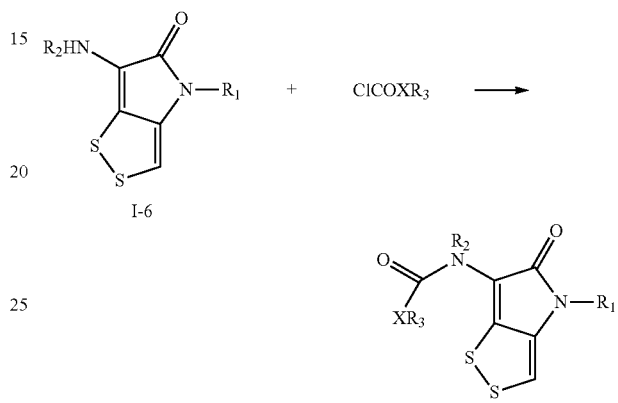

Wherein, X, R1, R2, R3 and R4 are the same as the definition below,

Wherein the dithiolopyrrolone compounds (Formula I) are chosen from

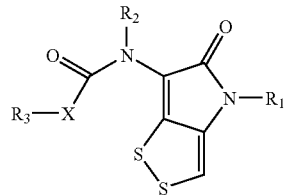

Wherein, X is O, NR$_4$ or S;

R$_1$ represents unsubstituted or optionally substituted following groups: C$_3$-C$_8$ cycloalkyl, C$_5$-C$_{10}$ aryl or three to ten-membered heterocyclic group having one to three heteroatoms independently selected from N, 0 or S;

R$_2$ represents hydrogen or C$_1$-C$_{10}$ alkyl;

R$_3$ represents hydrogen, or unsubstituted or optionally substituted following groups: C$_1$-C$_{10}$ alkyl, C$_2$-C$_{10}$ alkenyl, C$_2$-C$_{10}$ alkynyl, C$_3$-C$_{10}$ cycloalkyl, C$_1$-C$_{10}$ alkyl substituted by C$_5$-C$_{10}$ aryl, C$_5$-C$_{10}$ aryl, or three to ten-membered heterocyclic having one to three heteroatoms independently selected from N, O or S;

R$_4$ represents hydrogen or C$_1$-C$_{10}$ alkyl.

11. The process according to claim 10, wherein the molar ratio of the compound shown as formula I-6 and chloroformate or chlorine formamide is 1:1~1:10.

12. The process according to claim 10, wherein the organic base is triethylamine and/or pyridine.

13. The process according to claim 10, wherein the reaction is performed at the temperature between -20 and 50° C.

14. A process for preparing dithiolopyrrolone compounds (Formula I) or their pharmaceutically acceptable salts, including the following steps:

(1) Compound shown as formula II is prepared from the reaction between the compound shown as formula I-6 and carbonyl chloride or bis(trichloromethyl)carbonate via organic base in the non-protonic solvent;

(2) Reaction is carried out between the compound shown as formula II and $R_3XH$ via organic base in the non-protonic solvent,

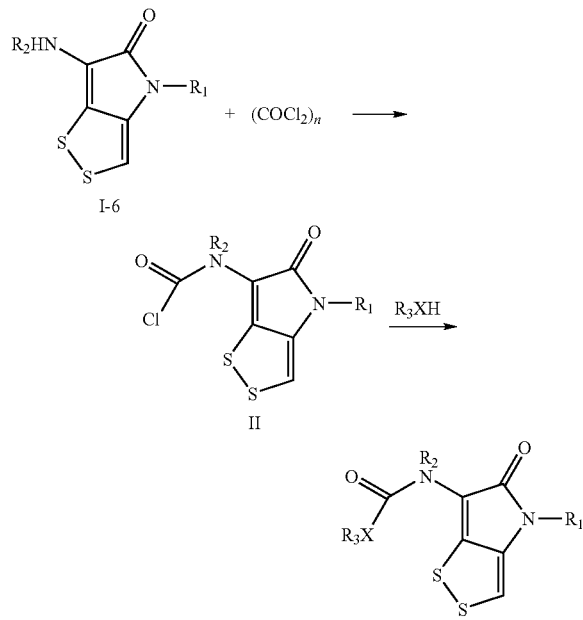

Wherein, X, $R_1$, $R_2$, $R_3$ and $R_4$ are the same as the definition below, and n is one or three, Wherein the dithiolopyrrolone compounds (Formula I) are chosen from

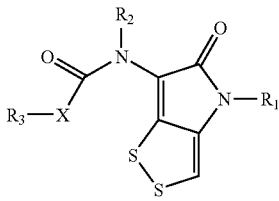

Wherein, X is O, $NR_4$ or S;

$R_1$ represents unsubstituted or optionally substituted following groups: $C_3$-$C_8$ cycloalkyl, $C_5$-$C_{10}$ aryl or three to ten-membered heterocyclic group having one to three heteroatoms independently selected from N, O or S;

$R_2$ represents hydrogen or $C_1$-$C_{10}$ alkyl;

$R_3$ represents hydrogen, or unsubstituted or optionally substituted following groups: $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkyl substituted by $C_5$-$C_{10}$ aryl, $C_5$-$C_{10}$ aryl, or three to ten-membered heterocyclic having one to three heteroatoms independently selected from N, O or S;

$R_4$ represents hydrogen or $C_1$-$C_{10}$ alkyl.

15. The process according to claim 14, wherein in step 1 molar ratio of the compound shown as formula I-6 and carbonyl chloride or bis(trichloromethyl)carbonate is 1:1~1:10.

16. The process according to claim 14, wherein in step 2 usage of $R_3XH$ is 1~10-folds of the molar amount of I-6.

17. The process according to claim 14, wherein in step (1) and/or step (2), the reaction is performed at temperature between −20 and 50° C.

18. The process according to claim 14, wherein in step (1) and/ or step (2), the organic base is triethylamine and/or pyridine.

19. The process according to claim 10, wherein the reaction time is detected by TLC.

20. Pharmaceutical compositions that contain dithiolopyrrolone compounds as shown as formula I or their pharmaceutically acceptable salts, Wherein the dithiolopyrrolone compounds (Formula I) are chosen from

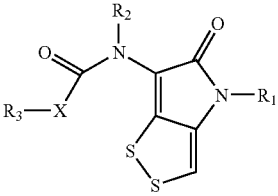

Wherein, X is O, $NR_4$ or S;

$R_1$ represents unsubstituted or optionally substituted following groups: $C_3$-$C_8$ cycloalkyl, $C_5$-$C_{10}$ aryl or three to ten-membered heterocyclic group having one to three heteroatoms independently selected from N, O or S;

$R_2$ represents hydrogen or $C_1$-$C_{10}$ alkyl;

$R_3$ represents hydrogen, or unsubstituted or optionally substituted following groups: $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkyl substituted by $C_5$-$C_{10}$ aryl, $C_5$-$C_{10}$ aryl, or three to ten-membered heterocyclic having one to three heteroatoms independently selected from N, O or S;

$R_4$ represents hydrogen or $C_1$-$C_{10}$ alkyl.

21. A method of elevating white blood cells comprising:
administering a therapeutically effective amount of at least one compound selected from the dithiolopyrrolone compounds as shown as formula I and their pharmaceutically acceptable salts Wherein the dithiolopyrrolone compounds (Formula I) are chosen from

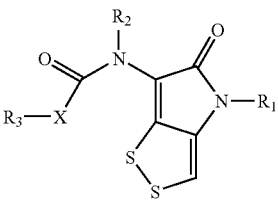

Wherein, X is O, $NR_4$ or S;

$R_1$ represents unsubstituted or optionally substituted following groups: $C_3$-$C_8$ cycloalkyl, $C_5$-$C_{10}$ aryl or three to ten-membered heterocyclic group having one to three heteroatoms independently selected from N, O or S;

$R_2$ represents hydrogen or $C_1$-$C_{10}$ alkyl;

$R_3$ represents hydrogen, or unsubstituted or optionally substituted following groups: $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkyl substituted by $C_5$-$C_{10}$ aryl, $C_5$-$C_{10}$ aryl, or three to ten-membered heterocyclic having one to three heteroatoms independently selected from N, O or S;

$R_4$ represents hydrogen or $C_1$-$C_{10}$ alkyl.

22. The method according to claim 21, wherein the white blood cells are neutrophils.

23. A method of inhibiting the reduction of peripheral white blood cells in the radiotherapy or chemotherapy comprising administering a therapeutically effective amount of at least one compound selected from the dithiolopyrrolone compounds as shown as formula I their pharmaceutically acceptable salts Wherein the dithiolopyrrolone compounds (Formula I) are chosen from

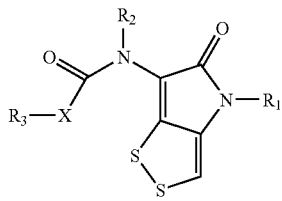

Wherein, X is O, $NR_4$ or S;
$R_1$ represents unsubstituted or optionally substituted following groups: $C_3$-$C_8$ cycloalkyl, $C_5$-$C_{10}$ aryl or three to ten-membered heterocyclic group having one to three heteroatoms independently selected from N, O or S;

$R_2$ represents hydrogen or $C_1$-$C_{10}$ alkyl;

$R_3$ represents hydrogen, or unsubstituted or optionally substituted following groups: $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkyl substituted by $C_5$-$C_{10}$ aryl, $C_5$-$C_{10}$ aryl, or three to ten-membered heterocyclic having one to three heteroatoms independently selected from N, O or S;

$R_4$ represents hydrogen or $C_1$-$C_{10}$ alkyl.

24. The method according to claim 23, wherein the white blood cells are neutrophils.

* * * * *